United States Patent
Tezel et al.

(10) Patent No.: US 10,232,129 B2
(45) Date of Patent: Mar. 19, 2019

(54) INJECTION DEVICE

(75) Inventors: Ahmet Tezel, Goleta, CA (US); Kevin McNerney, Huntington Beach, CA (US); Christopher S. Mudd, Goleta, CA (US); Blake R. Storie, Laguna Niguel, CA (US); Bastien Mandaroux, Cran Gevrier (FR)

(73) Assignee: Allergan, Inc., Irvine, CA (US)

( * ) Notice: Subject to any disclaimer, the term of this patent is extended or adjusted under 35 U.S.C. 154(b) by 775 days.

(21) Appl. No.: 12/629,480

(22) Filed: Dec. 2, 2009

(65) Prior Publication Data
US 2010/0152679 A1    Jun. 17, 2010

Related U.S. Application Data

(60) Provisional application No. 61/139,430, filed on Dec. 19, 2008, provisional application No. 61/119,298, filed on Dec. 2, 2008.

(51) Int. Cl.
*A61M 5/34* (2006.01)
*A61M 5/32* (2006.01)

(52) U.S. Cl.
CPC .......... *A61M 5/347* (2013.01); *A61M 5/3293* (2013.01); *A61M 2210/04* (2013.01)

(58) Field of Classification Search
CPC ...... A61M 5/3293; A61M 5/347; A61M 5/34; A51M 5/343
USPC .............................................. 604/240–241
See application file for complete search history.

(56) References Cited

U.S. PATENT DOCUMENTS

| 2,737,946 | A | 3/1956 | Hein, Jr. |
| 2,853,070 | A | 9/1958 | Maurice |
| D202,754 | S | 11/1965 | Naftolin |
| D214,112 | S | 5/1969 | Langdon |
| D224,066 | S | 6/1972 | McDonald |

(Continued)

FOREIGN PATENT DOCUMENTS

| EP | 0362484 | 4/1990 |
| EP | 1051988 A2 * | 11/2000 |

(Continued)

OTHER PUBLICATIONS

Davidenko et al., "Collagen-hyaluronic acid scaffolds for adipose tissue engineering", ACTA Biomaterialia, vol. 6, No. 10, Oct. 1, 2010, pp. 3957-3968, XP055055114.

(Continued)

*Primary Examiner* — Rebecca E Eisenberg
*Assistant Examiner* — Weng Lee
(74) *Attorney, Agent, or Firm* — Nathan S. Smith; Morgan, Lewis & Bockius LLP

(57) ABSTRACT

An injection device includes a syringe having a body with a piston disposed therein with an open end along with a viscous fluid disposed in the body for injection by the piston. A needle assembly is provided which includes a cannula having a luer connection engageable with the syringe distal end with the luer connector including a hub. Mating engagement is provided by way of internal threads at the syringe distal end and external threads of a hub with a pitch sufficient to prevent detachment of the hub from the syringe distal end during ejection of the viscous fluid. In addition, a stepped cavity, disposed in the hub, further prevents detachment of the hub from the syringe distal end during ejection of the viscous fluid.

26 Claims, 2 Drawing Sheets

(56) References Cited

U.S. PATENT DOCUMENTS

| | | | |
|---|---|---|---|
| 3,720,211 A | 3/1973 | Kyrias | |
| 3,807,048 A | 4/1974 | Malmin | |
| 4,240,423 A | 12/1980 | Akhavi | |
| 4,240,426 A * | 12/1980 | Akhavi | A61M 5/343 604/243 |
| 4,273,122 A | 6/1981 | Whitney et al. | |
| 4,326,517 A | 4/1982 | Whitney et al. | |
| 4,529,401 A | 7/1985 | Leslie et al. | |
| 4,699,612 A | 10/1987 | Hamacher | |
| D303,010 S | 8/1989 | Jabbusch | |
| 4,869,717 A | 9/1989 | Adair | |
| 5,024,656 A | 6/1991 | Gasaway et al. | |
| 5,046,506 A | 9/1991 | Singer | |
| 5,100,390 A | 3/1992 | Lubeck et al. | |
| 5,104,375 A | 3/1992 | Lubeck et al. | |
| 5,127,436 A | 7/1992 | Campion et al. | |
| 5,141,496 A | 8/1992 | Dalto et al. | |
| 5,295,980 A | 3/1994 | Ersek | |
| 5,305,788 A | 4/1994 | Mayeux | |
| 5,322,511 A | 6/1994 | Armbruster et al. | |
| 5,344,407 A | 9/1994 | Ryan | |
| 5,383,851 A | 1/1995 | Mackinnon, Jr. et al. | |
| 5,405,330 A | 4/1995 | Zunitch et al. | |
| D378,939 S | 4/1997 | Smith et al. | |
| 5,690,618 A | 11/1997 | Smith et al. | |
| 5,817,033 A * | 10/1998 | DeSantis | A61B 10/0275 600/562 |
| 5,964,737 A * | 10/1999 | Caizza | A61M 5/34 604/187 |
| D424,194 S | 5/2000 | Holdaway et al. | |
| D441,077 S | 4/2001 | Garito et al. | |
| 6,231,552 B1 * | 5/2001 | Jentzen | 604/241 |
| 6,432,046 B1 | 8/2002 | Yarush et al. | |
| 6,595,960 B2 * | 7/2003 | West et al. | 604/181 |
| 6,613,010 B2 | 9/2003 | Castellano | |
| 6,616,448 B2 | 9/2003 | Friedman | |
| D483,116 S | 12/2003 | Castellano | |
| 6,689,095 B1 | 2/2004 | Garitano et al. | |
| 6,783,514 B2 | 8/2004 | Tovey et al. | |
| 6,824,526 B2 | 11/2004 | Castellano | |
| 7,018,356 B2 | 3/2006 | Wise et al. | |
| 7,419,472 B2 | 9/2008 | Hibner et al. | |
| 7,494,473 B2 | 2/2009 | Eggers et al. | |
| D615,192 S | 5/2010 | Mudd et al. | |
| 7,878,981 B2 | 2/2011 | Strother et al. | |
| D637,287 S | 5/2011 | Mudd et al. | |
| 8,029,460 B2 | 10/2011 | Rush et al. | |
| 8,066,629 B2 | 11/2011 | Dlugos | |
| 8,480,630 B2 | 7/2013 | Mudd et al. | |
| 8,603,028 B2 | 12/2013 | Mudd et al. | |
| 2002/0010433 A1 * | 1/2002 | Johnson | A61M 5/347 604/241 |
| 2002/0151843 A1 | 10/2002 | Correa et al. | |
| 2003/0144632 A1 | 7/2003 | Hommann et al. | |
| 2003/0199883 A1 | 10/2003 | Laks | |
| 2004/0015133 A1 | 1/2004 | Karim | |
| 2004/0092927 A1 | 5/2004 | Podhajsky et al. | |
| 2004/0147883 A1 | 7/2004 | Tsai | |
| 2004/0220532 A1 * | 11/2004 | Caizza | A61M 5/3216 604/264 |
| 2005/0085767 A1 | 4/2005 | Menassa | |
| 2005/0131353 A1 | 6/2005 | Mossanen-Shams et al. | |
| 2005/0137496 A1 | 6/2005 | Walsh et al. | |
| 2005/0261633 A1 | 11/2005 | Khalaj | |
| 2006/0079765 A1 | 4/2006 | Neer | |
| 2006/0089594 A1 | 4/2006 | Landau | |
| 2007/0083155 A1 | 4/2007 | Muller | |
| 2007/0100363 A1 | 5/2007 | Dollar et al. | |
| 2007/0212385 A1 | 9/2007 | David | |
| 2007/0250010 A1 | 10/2007 | Hohlfelder et al. | |
| 2008/0033347 A1 | 2/2008 | D'Arrigo et al. | |
| 2008/0097325 A1 | 4/2008 | Tanaka et al. | |
| 2008/0108952 A1 | 5/2008 | Horvath et al. | |
| 2008/0188816 A1 * | 8/2008 | Shimazaki | A61M 5/34 604/240 |
| 2008/0200758 A1 | 8/2008 | Orbay et al. | |
| 2009/0088703 A1 * | 4/2009 | Azar | A61M 35/003 604/246 |
| 2009/0124996 A1 | 5/2009 | Heneveld et al. | |
| 2009/0143746 A1 | 6/2009 | Mudd et al. | |
| 2009/0240200 A1 | 9/2009 | Heneveld et al. | |
| 2009/0299328 A1 | 12/2009 | Mudd et al. | |
| 2010/0069848 A1 | 3/2010 | Alferness et al. | |
| 2010/0152675 A1 | 6/2010 | McClintock | |
| 2010/0280488 A1 | 11/2010 | Pruitt et al. | |
| 2010/0282774 A1 | 11/2010 | Greter et al. | |
| 2011/0021905 A1 | 1/2011 | Patrick et al. | |
| 2011/0092916 A1 | 4/2011 | Tezel et al. | |
| 2011/0137286 A1 | 6/2011 | Mudd et al. | |
| 2011/0160674 A1 | 6/2011 | Holmes et al. | |
| 2013/0131632 A1 | 5/2013 | Mudd et al. | |
| 2013/0131633 A1 | 5/2013 | Mudd et al. | |
| 2013/0274670 A1 | 10/2013 | Mudd et al. | |

FOREIGN PATENT DOCUMENTS

| | | |
|---|---|---|
| EP | 1051988 A2 | 11/2000 |
| EP | 1486218 | 12/2004 |
| EP | 1859827 | 11/2007 |
| EP | 1923086 A1 | 5/2008 |
| EP | 2335755 | 6/2011 |
| FR | 2622457 | 5/1989 |
| WO | WO 1999/048601 | 9/1999 |
| WO | 2005095225 | 10/2005 |
| WO | WO 2008/019265 A2 | 2/2008 |
| WO | WO 2008/079824 | 7/2008 |
| WO | WO 2009/098666 | 8/2009 |
| WO | WO 2009/158145 | 12/2009 |

OTHER PUBLICATIONS

Park et al., "Biological characterization of EDC-crosslinked collagen-hyaluronic acid matrix in dermal tissue restoration", Biomaterials, Elsevier Science Publishiers BV, vol. 24, No. 9, Apr. 1, 2003, pp. 1631-1641, XP004404219.

Wang et al., "In vivo stimulation of de novo collagen production caused by cross-linked hyaluronic acid dermall filler injections in photodamaged human skin.", Archives of Dermatology, American Medical Association, US, vol. 143, No. 2, Feb. 1, 2007, pp. 155-163, XP002574140.

* cited by examiner

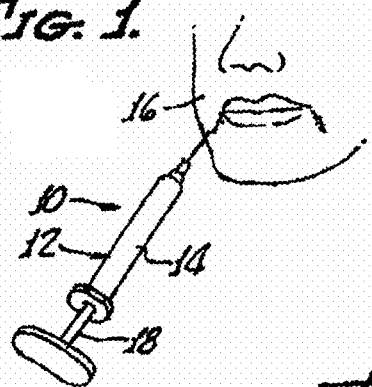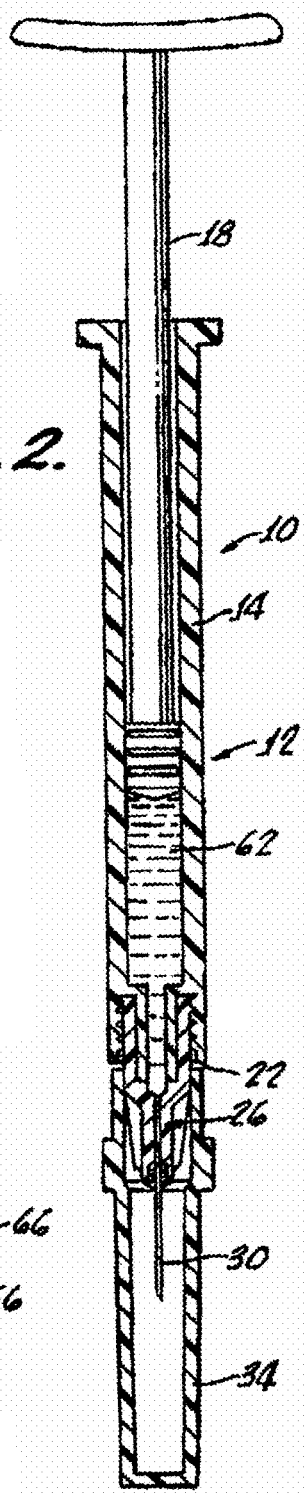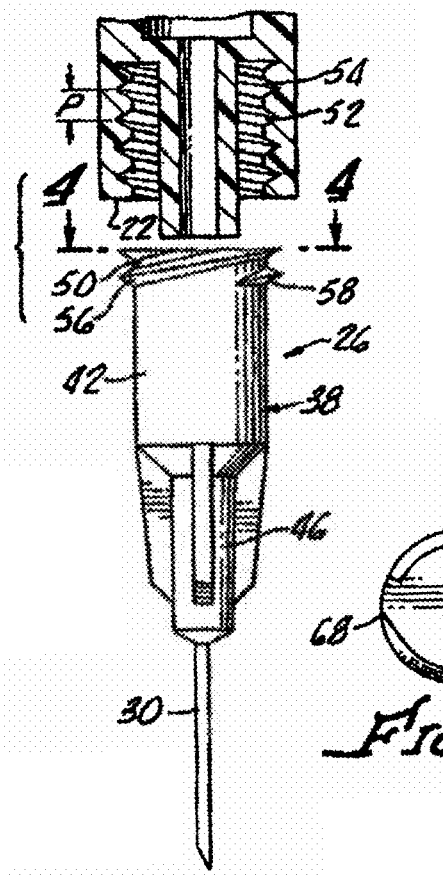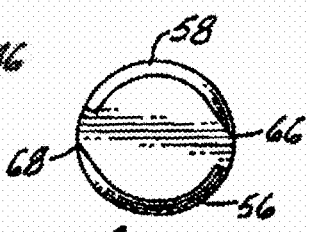
FIG. 1.
FIG. 2.
FIG. 3.
FIG. 4.

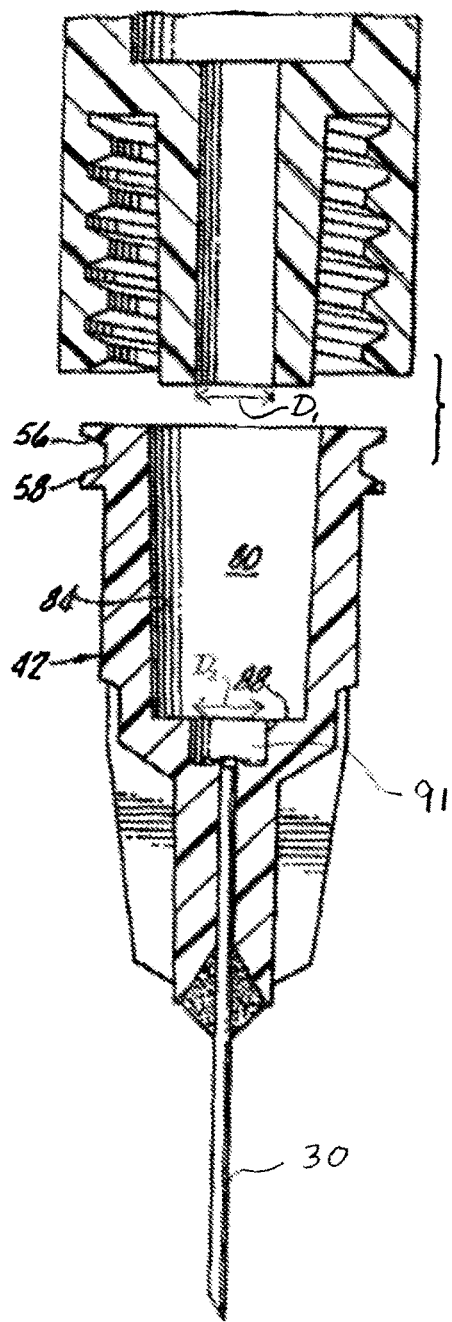
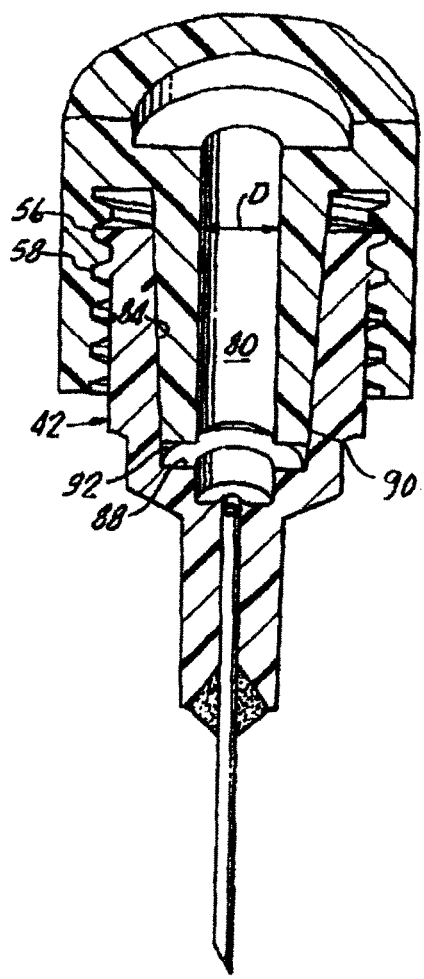

INJECTION DEVICE

RELATED APPLICATIONS

This application claims the benefit of U.S. Provisional Patent Application No. 61/119,298, filed on Dec. 2, 2008 and U.S. Provisional Patent Application No. 61/139,430, filed on Dec. 19, 2008, the entire disclosure of each of which is incorporated herein by this specific reference.

BACKGROUND

The present invention is generally directed to non-surgical devices for the correction of skin contour defects and aging and is more particularly directed to an injection device for enabling introduction of a dermal filler into peripheral locations of a human body through a cannula.

Dermal fillers such as, such as Juvederm™, a hyaluronic acid based formulation, have been used for the treatment of nasal labial folds, lip augmentation, tear troughs, and for facial volumizing through the use of very fine syringe needles.

The dermal fillers are of high viscosity and this provides for effective, and preferably substantially uniform, suspension of the dermal filler into a peripheral location.

A relatively small needle size, gauge, is preferred for delivery of the dermal filler in order to lessen complications and recovery time. However, in combination with the relatively high viscosity of the dermal filler, a problem can arise with regard to needle assembly separation from the syringe due to the high pressure generated by a piston reacting on the high viscosity dermal filler in order to eject the filler from the syringe through a fine needle and into the patient.

The present invention overcomes this problem by providing an ejection device which eliminates, or substantially reduces, the probability of needle assembly/syringe separation during a procedure.

SUMMARY OF THE INVENTION

An injection device in accordance with the present invention generally includes a syringe having a body with a piston disposed therein and an open distal end.

A needle assembly is provided which includes a cannula and a luer connector engagable with the syringe distal end. The needle or cannula, hereinafter "cannula", has a gauge of about 18 to a gauge of about 25 or greater. The luer connector includes a hub with a distal end supporting the cannula and a proximal end matable with the syringe distal end.

In one embodiment, the present invention further includes a viscous fluid, for example, a hyaluronic acid-based dermal filler, disposed in the syringe's body and which is injectable by the piston into a peripheral location of a human or animal body through the cannula.

The mating engagement, for example, between the hub and the syringe distal end is provided by internal threads disposed in the syringe distal end and external threads disposed on the hub, as well as between a tapered syringe cone and a tapered inside surface of the hub. The internal threads have a pitch which is sufficient to prevent detachment of the hub from syringe distal end during injection of the viscous fluid into a peripheral location of a human or animal body.

More particularly, in one embodiment, the internal threads have a pitch of between about 2 mm and about 5 mm. For example, the internal threads have a pitch of about 3 mm.

The internal thread may be double lead screw threads. In addition, the external threads disposed on the hub further may also be double lead screw threads and the double lead screw threads provide an advantage of enabling the hub to travel twice the distance into mating engagement with the syringe distal end with each single turn of the hub. In other embodiments, the internal threads have a pitch of about 2.0 mm, about 3.0 mm, about 3.5 mm, about 4 mm, about 4.5 mm or about 5 mm. In addition, the external threads may have a pitch of about 2.0 mm, about 3.0 mm, about 3.5 mm, about 4 mm, about 4.5 mm or about 5 mm.

In a specific embodiment, the external threads comprise single circumference double lead screw threads as will be hereinafter described in greater detail.

In addition, a cavity, for example, a stepped cavity, is disposed in the hub. The cavity serves not only reduces dead space in the syringe but also significantly reduces the possibility of detachment of the hub from the syringe distal end during operation of the piston to eject the viscous fluid through the cannula. Thus, the cavity can be considered a hub retention cavity.

BRIEF DESCRIPTION OF THE DRAWINGS

The advantages and features of the present invention will be better understood by the following description when considered in conjunction with the accompanying drawings in which:

FIG. 1 is an illustration of use of an injection device in accordance with the present invention for injecting a viscous fluid into a peripheral location of the human, generally showing a syringe having a body with a piston and a needle assembly;

FIG. 2 is a cross sectional view of the syringe shown in FIG. 1 illustrating more clearly showing the syringe body along with a needle assembly with a luer connector engagable with a distal end of the syringe along with a viscous fluid disposed in the syringe body;

FIG. 3 is an enlarged cross sectional view of the mating engagement between a luer connector hub and a distal end of the syringe specifically illustrating internal threads disposed in the syringe distal end and external threads along the hub for enabling the mating engagement, along with a cavity disposed in the hub configured as a hub retention cavity;

FIG. 4 is end view of the hub illustrating double lead screws;

FIG. 5 is an enlarged cross section view of the needle assembly and an open distal end of the syringe body showing a tapered syringe cone engageable with a tapered inside surface of the needle assembly hub; and FIG. 6 is a cross-section view of the needle assembly engaged with the syringe's open distal end.

DETAILED DESCRIPTION

With reference to FIG. 1, there is shown an injection device 10 in accordance with the present invention having a syringe 12 with a body 14 with a piston 18 disposed therein.

With additional reference to FIGS. 2 and 3, the syringe 12 includes an open distal end 22, and a needle assembly 26. The needle assembly includes a cannula 30 along with a sheath 34 and a luer connector 38 engagable with the syringe open distal end 22, which includes a hub 42 having a distal end 46 and a proximal end 50 matable with the syringe distal end 22.

Internal threads 52, 54 and external threads 56, 58 enable the mating engagement. Pitch (P) of the threads 52, 54 enables the ejection of viscous fluid 62 through the cannula 30 upon operation of the piston 18 without separation of the hub 42 from the syringe open distal end 22 during ejection of the viscous fluid 62 as illustrated in FIG. 1.

In some embodiments, the viscous fluid 62 is a dermal filler. In some embodiments, the viscous fluid is a hyaluronic acid-based fluid having a viscosity between about 50,000 cps and about 500,000 cps, measured at about 25° C. with a controlled stress rheometer (RS600 TA Instrument) and a cone plate geometry (40 mm, 2°). In some embodiments, the viscous fluid is a hyaluronic acid based dermal filler having a viscosity greater than about 130,000 cps.

When measured with a traction column test (Versatest, Mecmesin), at 13 mm/min (extrusion speed) and a needle with a gauge between 21 G to 32 G, the viscous fluid may have an extrusion force of between about 5N up to about 200N, more specifically, an extrusion force of between about 10N to about 150N.

In an exemplary embodiment, the pitch of the hub threads 56, 58 is between about 2 mm and about 5 mm. Preferably, the pitch is about 3 mm. The threads 52, 54 and 56, 58 are preferably at least double lead screw threads, although triple, and even quadruple lead threads may used. As most clearly shown in FIG. 4, in one particular embodiment, the threads 56, 58 have two thread starts 66, 68 at a 180° radial displacement from one another.

As hereinabove noted, this enables rapid engagement of the hub 42 with the syringe open distal end 22.

In one embodiment, the hub 42 is formed from a low elasticity material, for example, an acrylic or a polycarbonate, rather than polypropylene typically used for syringe hubs, as hereinafter described in connection with needle retention tests. This further enhances the prevention of detachment of the hub 46 from the syringe open distal end 22.

With reference to FIGS. 5 and 6, hub 42 includes a hub retention cavity 80 defined by an inside surface 84 of the hub 42 and a step 88, thus providing a unique stepped interior surface. As shown in FIG. 5, the step 88 extends normal to the inside surface 84 of the hub. When torqued to the syringe and maximally seated as shown in FIG. 6, a tapered syringe cone 90 stops short of the step 88 and creates a dead space 92 which is reduced by the step 88. Engagement between the cone 90 and inside surface 84, which is also tapered, provides a seal therebetween. Low dead space reduces the amount of fluid that cannot be administered. This is important in that the fluids to be administered, by injection, often are very expensive.

The step 88 unexpectedly prevents or substantially reduces the possibility of detachment of the hub 42 from the syringe cone 90 and syringe open distal end 22 during injection of the viscous fluid 62.

That is, the average detachment force is significantly greater with the step 88 formed in the cavity hub retention cavity 80 of the hub 42 as was discovered during comparison study as follows:

Test methods used in this study utilized equipment designed by Omnica Corporation specifically for torque setting and detachment testing.

The torque set unit utilizes a numerically controlled motor and torque sensor which tightens the needle hub 42 onto the syringe open distal end 22 and a pre-determined torque setting testing is shown that the static friction between the needle hub 42 and the syringe open distal end 22 materials causes more overshoot than observed with standard polypropylene hubs (not shown).

A detachment tester utilizes a numerically controlled motor driving linear carriage against a forced transducer.

In a comparison test, all of the hubs (not shown) were attached to the syringe open distal end 22 and cone 90 with a torque of 0.07 Nm (Newton meter). All of the tests were performed on 0.8 cc syringes having identical dimensions, for example, syringe open distal end 22 having an entry diameter D (see FIG. 6), of about 4 mm.

The results are shown in Table 1 for nominal torque static test needle retention with various design attribute combinations.

Table 1 shows that the conventional polypropylene hub mated to a syringe with 5 mm threads has an average detachment force 46.1 N (Newton) when the hub is attached to the syringe with a force of 0.07 Nm.

TABLE 1

Nominal torque Static Test Needle Retention with Various Design Attribute Combinations

| Needle Design | Average Detachment Force (N)[1] @ 0.07 Nm |
| --- | --- |
| Conventional Polypropylene Hub, Syringe with 5 mm Threads | 46.1 |
| Conventional Polypropylene Hub, Syringe with 3 mm Threads | 56.2 |
| Polycarbonate Hub and Syringe with 5 mm Threads | 83.2 |
| Polycarbonate Hub and Syringe with 3 mm Threads | 96.0 |
| Polycarbonate Hub and Syringe with 3 mm Threads and Stepped Cavity | 200+ |

Slight improvement shown in the conventional polypropylene hub attached to the syringe body with 3 mm threads, and an average detachment force of about 56.2 N.

Utilizing polycarbonate instead of polypropylene for the hub 42 results in an average detachment force of 83.2 N with 5 mm threads utilized for attachment.

Combination of polycarbonate hub 42 with 3 mm threads without a step 88 results in a 96 N average detachment force.

Surprisingly, the detachment force for the hub 42 with 3 mm threads incorporating the dead space reducing step 88 results in an average detachment force of more than 200 N.

It is contemplated that other structures may be useful in reducing dead space in a manner effective to increase detachment force relative to conventional syringe/needle combinations. For example, it is contemplated that reduced dead space can be accomplished, within the scope of the present invention, by reducing an outer diameter of the syringe luer tip, increasing an inner diameter of the hub cavity, and/or other ways effective to increase the engagement length of the syringe tip and the hub.

EXAMPLE

A multi-center, double-blind, randomized parallel-controlled prospective comparison study was undertaken to test needle disengagement rates. This study tested needle disengagement rates of a Polycarbonate Hub and Syringe with 3 mm Threads and Stepped Cavity in accordance with the present invention (study device) in comparison to a conventional polypropylene hub and syringe with 5 mm threads (conventional device). Needles of each of the conventional devices and the study devices tested were all 30 G×½" needles. The material injected for the study was Juvederm™ Ultra Injectable Gel (dermal filler).

There were up to 288 study participants. Each study participant underwent treatment for improving his or her bilateral nasolabial folds using 2 syringes of dermal filler packaged in either the conventional device or the study device.

The results demonstrated a significant difference in needle disengagement rates between the conventional device and the study device. No disengagements were reported for the study device. Between 3% and 7% of the needles of the conventional device unintentionally disengaged during injection.

Although there has been hereinabove described a specific injection device in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. An injection device for delivering a dermal filler, the device comprising:
   a syringe having (i) a body with a piston disposed therein and (ii) an open distal end portion including a tapered syringe cone;
   a needle assembly comprising a cannula and a luer connector engageable with the syringe open distal end portion, said luer connector comprising a hub having an inner bore, the inner bore comprising a proximal retention section, a stepped section, and a cannula retention section, the proximal retention section being mateable with the syringe open distal end portion, the stepped section being smaller in diameter than the proximal retention section and being disposed intermediate the proximal retention section and the cannula retention section, the inner bore having a stepped section surface wherealong the inner bore decreases in diameter to a proximal end of a cannula retention surface of the cannula retention section, the inner bore not increasing in diameter from the proximal retention section to a distal end of the cannula retention section, the cannula retention section having a constant diameter, the cannula retention surface being mated against an outer surface of the cannula to secure the cannula within the cannula retention section; and
   internal threads disposed in the syringe open distal end portion and external threads disposed on said hub enabling mating engagement between the hub and the syringe open distal end portion;
   said hub having an inside surface of the proximal retention section comprising a wall correspondingly tapered to said tapered syringe cone and that includes a step extending normal to the wall, the step being spaced apart from a distal-most surface of the tapered syringe cone in a distal direction when the hub and the syringe cone are maximally seated thereby reducing dead space within the proximal retention section for preventing detachment of the hub from the tapered syringe cone during injection of a dermal filler contained in the syringe body.

2. The device according to claim 1, wherein the internal threads have a pitch of between about 2 mm and about 5 mm.

3. The device according to claim 2, wherein the internal threads have a pitch of about 3 mm.

4. The device according to claim 3, wherein the external threads comprise double lead screw threads.

5. The device according to claim 1, wherein the external threads comprise single circumference double lead screw threads.

6. The device according to claim 1, further comprising a hyaluronic acid-based dermal filler contained in the syringe body and wherein the dermal filler has a viscosity of at least about 130,000 cps.

7. The device of claim 1, wherein the cannula has a gauge of greater than about 25 G.

8. The device of claim 1, wherein the cannula has a gauge between 21 G and 32 G.

9. The device of claim 1, wherein the hub comprises polycarbonate and the syringe internal threads have a pitch of about 3 mm, and wherein when the hub is threadingly coupled to the syringe at a torque of 0.07 Nm, a detachment force of the hub from the syringe exceeds 200 Newtons.

10. The device of claim 1, wherein the cannula retention surface extends normal to the stepped section surface.

11. The device of claim 1, wherein the cannula retention surface extends continuously with the stepped section surface.

12. The device of claim 1, wherein the outer surface of the cannula is mated against the cannula retention surface from the proximal end of the cannula retention surface to the distal end of the hub.

13. The device of claim 1, wherein the stepped section has a constant diameter.

14. A needle assembly for an injection device for facilitating delivery of a dermal filler, the assembly comprising:
   a needle hub comprising an inner bore and a longitudinal axis, the inner bore having a proximal retention section, an intermediate section, and a cannula retention section, the proximal retention section having a tapered inner surface and a proximal step whereat the inner bore decreases in diameter to the intermediate section, the proximal step being formed by an intersection of a wall surface of the proximal retention section and an inner surface of the intermediate section, the wall surface of the proximal retention section extending perpendicular relative to the longitudinal axis, the intermediate section having a cannula step whereat the inner bore decreases in diameter to a proximal end of the cannula retention section, the proximal step being interposed between the tapered inner surface and the cannula step, the inner bore not increasing in diameter from the proximal retention section to a distal end of the cannula retention section, the cannula retention section having a constant diameter, the cannula step being formed by an intersection of a wall surface of the intermediate section and a cannula engagement surface of the cannula retention section; and
   a cannula having a proximal portion seated against the cannula retention section;
   wherein the proximal retention section and the intermediate section, when coupled with a distal end portion of a syringe, collectively reduce dead space within the inner bore for preventing detachment of the hub from the syringe during an injection procedure.

15. The needle assembly of claim 14, further comprising a syringe having a distal end portion.

16. The needle assembly of claim 14, wherein the hub further comprises a luer connector engageable with a distal end portion of a syringe.

17. The needle assembly of claim 14, further comprising external threads disposed on the hub enabling mating engagement between the hub and internal threads of a distal end portion of a syringe.

18. The needle assembly of claim 17, wherein the external threads comprise double lead screw threads.

19. The needle assembly of claim 17, wherein the external threads comprise single circumference double lead screw threads.

20. The needle assembly of claim 14, wherein the hub comprises polycarbonate, and further comprising a syringe having internal threads that have a pitch of about 3 mm, and wherein when the hub is threadingly coupled to the syringe at a torque of 0.07 Nm, a detachment force of the hub from the syringe exceeds 200 Newtons.

21. The needle assembly of claim 14, wherein the cannula engagement surface extends normal to the intermediate section wall.

22. The needle assembly of claim 14, wherein the cannula retention surface extends continuously with the intermediate section wall.

23. The needle assembly of claim 14, wherein the proximal portion of the cannula is mated against the cannula retention surface from the proximal end of the cannula retention section to the distal end of the hub.

24. The needle assembly of claim 14, wherein the intermediate section has a constant diameter.

25. The needle assembly of claim 14, wherein the proximal retention section has a tapered diameter.

26. A needle assembly for an injection device for facilitating delivery of a dermal filler, the assembly consisting essentially of:
a needle hub comprising an inner bore and a longitudinal axis, the inner bore having a proximal retention section, an intermediate section, and a cannula retention section, the proximal retention section having a tapered inner surface and a proximal step whereat the inner bore decreases in diameter to the intermediate section, the proximal step being formed by an intersection of a wall surface of the proximal retention section and an inner surface of the intermediate section, the wall surface of the proximal retention section extending perpendicular relative to the longitudinal axis, the intermediate section having a cannula step whereat the inner bore decreases in diameter to a proximal end of the cannula retention section, the proximal step being interposed between the tapered inner surface and the cannula step, the inner bore not increasing in diameter from the proximal retention section to a distal end of the cannula retention section, the cannula retention section having a constant diameter, the cannula step being formed by an intersection of a wall surface of the intermediate section and a cannula engagement surface of the cannula retention section; and
a cannula having a proximal portion seated against the cannula retention section;
wherein the proximal retention section and the intermediate section, when coupled with a distal end portion of a syringe, collectively reduce dead space within the inner bore for preventing detachment of the hub from the syringe during an injection procedure.

* * * * *